US011331439B1

(12) United States Patent
Aqel

(10) Patent No.: US 11,331,439 B1
(45) Date of Patent: May 17, 2022

(54) NEEDLE ASSEMBLY

(71) Applicant: Fadi Aqel, Burbank, IL (US)

(72) Inventor: Fadi Aqel, Burbank, IL (US)

( * ) Notice: Subject to any disclaimer, the term of this patent is extended or adjusted under 35 U.S.C. 154(b) by 55 days.

(21) Appl. No.: 16/888,518

(22) Filed: May 29, 2020

(51) Int. Cl.
*A61M 5/32* (2006.01)
*A61M 5/34* (2006.01)

(52) U.S. Cl.
CPC .......... *A61M 5/329* (2013.01); *A61M 5/3202* (2013.01); *A61M 5/3293* (2013.01); *A61M 5/345* (2013.01); *A61M 5/347* (2013.01)

(58) Field of Classification Search
CPC ...... A61M 5/329; A61M 5/345; A61M 5/347; A61M 5/3202; A61M 5/3293; A61M 5/3297; A61M 5/346; A61M 5/3271; A61M 2005/3228
See application file for complete search history.

(56) References Cited

U.S. PATENT DOCUMENTS

2019/0046735 A1* 2/2019 Ingerslev .......... A61M 5/31593

FOREIGN PATENT DOCUMENTS

WO    WO-2016116911 A1 * 7/2016 .............. A61M 5/32

* cited by examiner

*Primary Examiner* — Theodore J Stigell
*Assistant Examiner* — Rachel T. Smith
(74) *Attorney, Agent, or Firm* — The Law Offices of Komad Sherinian, LLC; Depeng Bi

(57) ABSTRACT

A needle assembly includes a needle, a rear needle cap and a front needle cap. The needle includes a needle hub and a needle shaft running through and attached to the needle hub. The shaft incorporates two sharp ends and an internal channel running through the entire length of the shaft. The needle hub includes a rear needle body and a front needle body. The rear needle cap is adapted to be attached to the rear needle body and the front needle cap is adapted to be attached to the front needle body. The front needle body incorporates a guiding channel and a locking receptacle connecting to and extending from the guiding channel in a needle detachment direction. The front needle cap includes an internal locking plug adapted to move along the guiding channel and be disposed inside the locking receptacle. The front needle cap also incorporates a funnel lip.

18 Claims, 3 Drawing Sheets

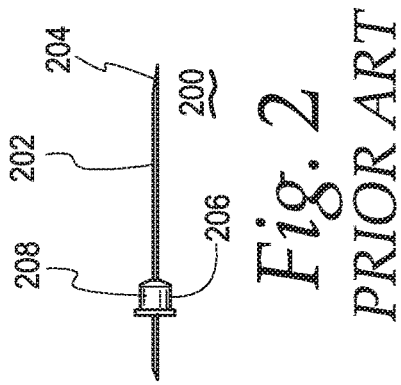
Fig. 2
PRIOR ART
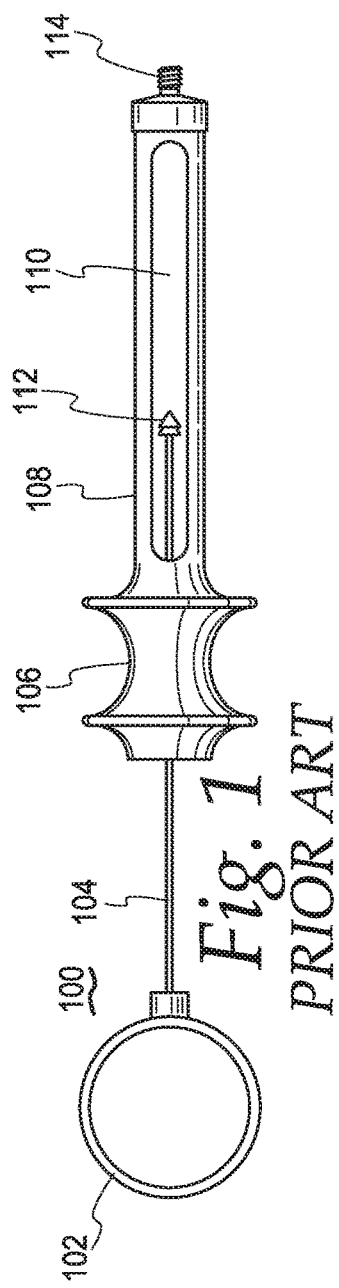
Fig. 1
PRIOR ART
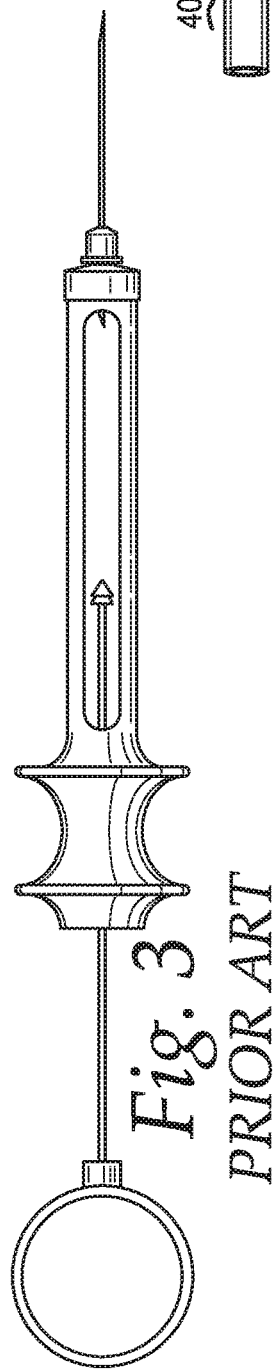
Fig. 3
PRIOR ART
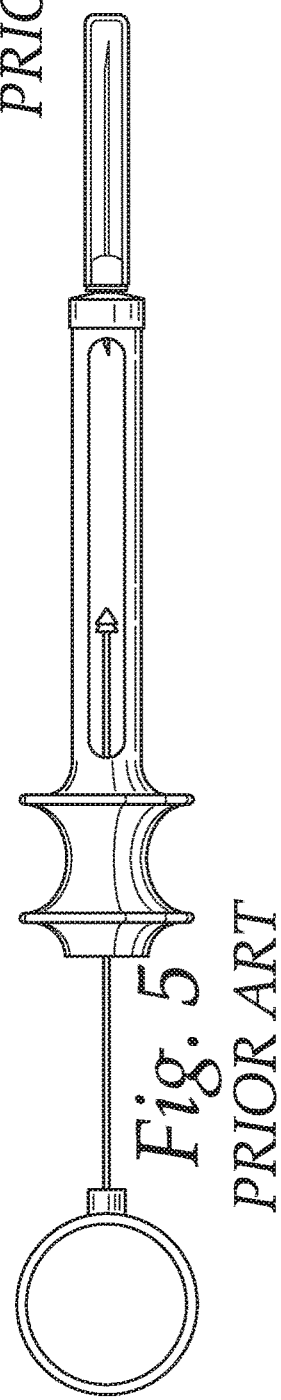
Fig. 4
PRIOR ART
Fig. 5
PRIOR ART

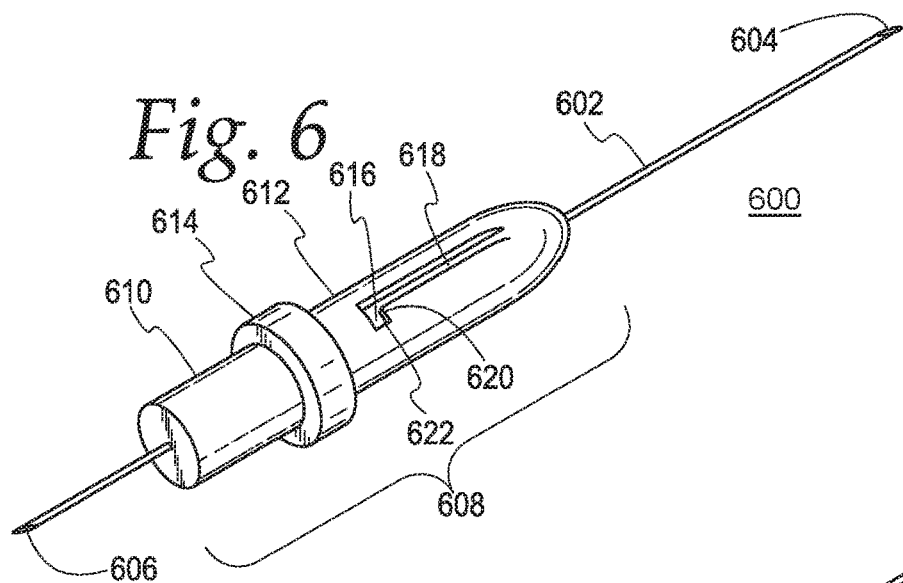
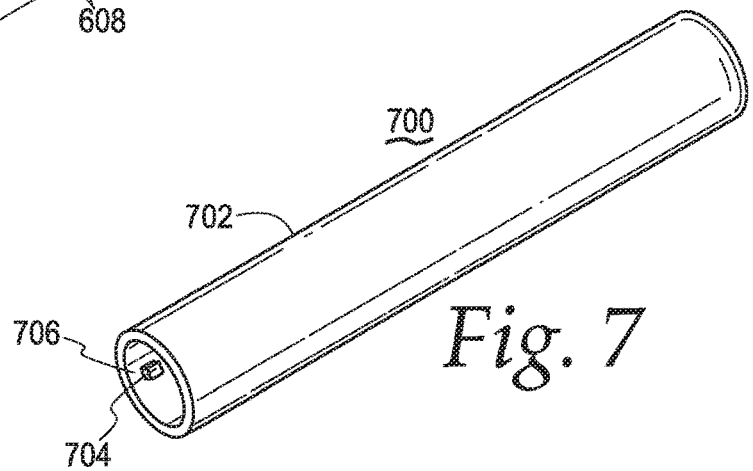
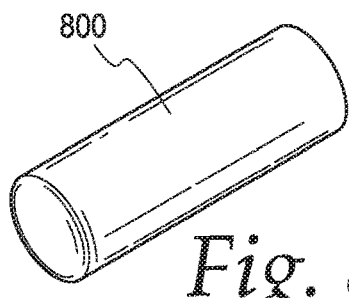
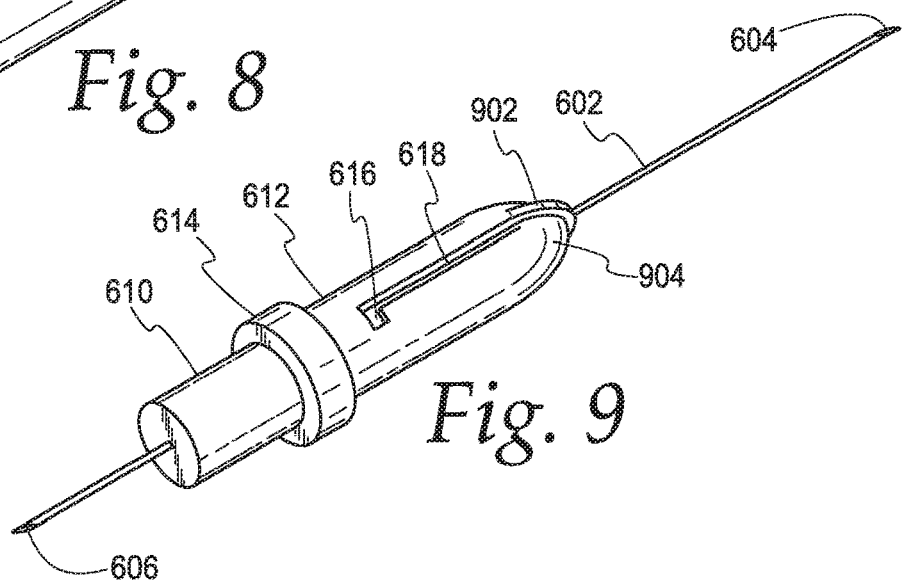

NEEDLE ASSEMBLY

CROSS REFERENCE TO RELATED APPLICATIONS

NONE.

FIELD OF THE DISCLOSURE

The present invention generally relates to medical devices, and more particularly relates to an improved needle assembly. More particularly still, the present disclosure relates to an improved needle assembly used with an aspirating syringe.

DESCRIPTION OF BACKGROUND

Aspirating syringes are widely used in medical and other fields. They are used for both injection and aspiration purposes. Needles are attached to aspirating syringes in practice. A prior art aspirating syringe is shown in FIG. 1 and indicated at 100. The aspirating syringe 100 includes a thumb ring 102, a plunger 104 connected to the thumb ring 102, a harpoon 112 at the opposite end of the piston 104, a finger grip 106, a barrel 108 connected to the finger grip 106, an opening 110 on the barrel 108 for receiving a cartridge (not shown), and a needle adaptor 114 at the opposite end of the barrel 108. The plunger 104 is received by an internal cavity of the finger grip 106 and the internal cavity of the barrel 108. A prior art needle is shown in FIG. 2 and indicated at 200. The needle 200 includes a needle hub 206 having a front body portion 208, and a shaft 202 running through the needle hub 206 and a front bevel 204. The aspirating syringe 100 with the needle 200 attached is shown in FIG. 3. A prior art front needle cap is shown in FIG. 4 and indicated at 400.

After the aspirating syringe 100 and the needle 200 are used in a particular medical situation, a user (such as a medical professional) first attaches the front needle cap 400 to the needle hub 206, and then removes the cap 400 and the needle 200 from the syringe 100. This process is also referred to as recapping. To do so, the user needs to align the needle bevel 204 with the opening of the front needle cap 400 before insert the bevel 204 and the shaft 202 into the internal cavity of the front needle cap 400. Though users are generally very careful with this operation, mishaps do happen when the alignment is not proper and the needle bevel 204 punctures the user's finger or other parts of the user's hand. Since the needle 200 may well have bacteria and/or viruses attached after having been removed from a patient's body, the mishaps can cause disastrous health issues to the user. Accordingly, there is a need for a new type of front needle caps.

After the shaft 202 is inside the front needle cap 400, the user pushes the front needle cap 400 against the needle hub 206 such that the front needle cap 400 receives the entirety of the front body 208. For example, the user uses her/his left hand to hold the barrel 108 and her/his right hand to operate the front needle cap 400. The prior art front needle cap 400 and the prior art front body 208 engage with each other via friction. The front body 208 is in a cylindrical shape.

Once the front needle cap 400 is attached to the front body 208, the user holds the cap 400 and tries to remove the needle 200 away from the aspirating syringe 100. For instance, when the needle adaptor 114 incorporates a thread and the needle hub 206 is attached to the aspirating syringe 100 by threading, the user rotates the front needle cap 400 counterclockwise. At the same time, the user applies some amount of force on the front needle cap 400 to pull it to the right of the user. In such a case, the front needle cap 400 can accidentally become disengaged from the needle body 208 since they are coupled together by friction alone. Furthermore, when the needle 200 is used in, for example, a dental procedure, the front needle body 208 may become wet. For instance, the patient's saliva may wet the front needle body 208. The moisture on the front needle body 208 makes it more likely for the front needle cap 400 to snap off the front needle body 208 while the needle 200 is still attached to the aspirating syringe 100.

The accidental separation of the front needle cap 400 from the needle 200 is more likely to happen to inexperienced users. When it happens, the entirety of the needle bevel 204 can be out of the internal cavity of the front needle cap 400. In the event of the separation, a reflex is likely to happen to the user's right hand holding the front needle cap 400 since a relatively strong force is required to remove the front needle cap 400 that is frictionally engaged with the needle hub 206. In other words, the user's right hand moves leftwards towards the needle bevel 204, and gets punctured by the needle bevel 204. Bacteria and/or viruses on the needle 200 then likely transmit to the user, and cause severe heath harm to her/him. Accordingly, there is a need for a new type of needles. Furthermore, there is a need for a new needle assembly including a needle and a needle cap.

SUMMARY OF THE DISCLOSURE

Generally speaking, pursuant to the various embodiments, the present disclosure provides a needle assembly. The needle assembly includes a needle, which includes a needle hub and a needle shaft disposed within and running through the needle hub. The needle hub includes a rear needle body and a front needle body. The rear needle body includes a needle coupling mechanism adapted for attaching the needle to a syringe needle adaptor. The shaft includes a sharp front end, a sharp rear end and an internal cavity channel extending the entire length of the shaft. The front needle body includes a guiding channel exposed on an outer surface of the front needle body. The front needle body includes a locking receptacle exposed on an outer surface of the front needle body, connecting to a rear end of the guiding channel and extending away from the guiding channel in a needle detachment direction. The needle assembly further includes a rear needle cap adapted to be attached to and enclose the rear needle body, and a front needle cap adapted to be attached to and enclose the front needle body. The front needle cap includes a front needle cap cavity and a locking plug. The locking plug extends away from an inner surface of the front needle cap and into the front needle cap cavity. The locking plug is adapted to move along the guiding channel and be received by the locking receptacle. The front needle cap further incorporates a front funnel lip. The needle coupling mechanism is a female thread or a male thread. The sharp front end is a bevel. The sharp rear end is a bevel. The locking plug and the locking receptacle are in a shape of a prism or a spherical cap.

Further in accordance with the present teachings is a needle assembly. The needle assembly includes a needle having a needle hub and a needle shaft disposed within and running through the needle hub. The needle hub includes a rear needle body and a front needle body. The rear needle body includes a needle coupling mechanism adapted for attaching the needle to a syringe needle adaptor. The shaft includes a sharp front end, a sharp rear end and an internal cavity channel extending the entire length of the shaft. The needle assembly further includes a rear needle cap adapted to be attached to and enclose the rear needle body, and a front needle cap adapted to be attached to and enclose the front needle body. The front needle cap incorporates a front needle cap cavity and a front funnel lip. The needle coupling mechanism is a female thread or a male thread. The sharp front end is a bevel and the sharp rear end is a bevel. The needle hub further includes a cap stopper disposed between the rear needle body and the front needle body.

BRIEF DESCRIPTION OF THE DRAWINGS

Although the characteristic features of this disclosure will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 1 is a perspective view of a prior art aspirating syringe.

FIG. 2 is a perspective view of a prior art needle for an aspirating syringe.

FIG. 3 is a perspective view of a prior art aspirating syringe with a prior art needle attached.

FIG. 4 is a perspective view of a prior art front needle cap.

FIG. 5 is a perspective view of a prior art aspirating syringe with a prior art needle and a prior art front needle cap attached.

FIG. 6 is a front perspective view of a new needle in accordance with the present teachings.

FIG. 7 is a front perspective view of a new front needle cap in accordance with this disclosure.

FIG. 8 is a front perspective view of a rear needle cap in accordance with this disclosure.

FIG. 9 is a front perspective view of a new needle in accordance with this disclosure.

Figure 10:
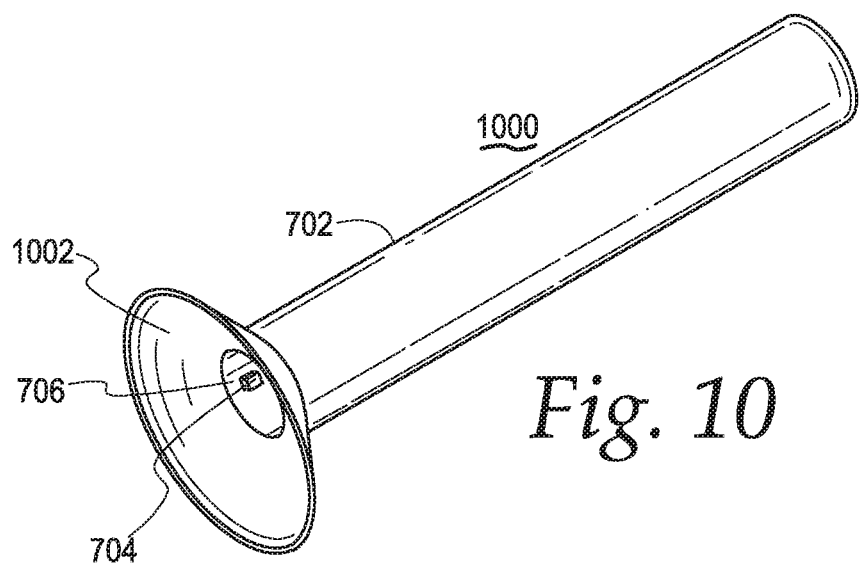
FIG. 10 is a front perspective view of a new front needle cap in accordance with this disclosure.

A person of ordinary skills in the art will appreciate that elements of the figures above are illustrated for simplicity and clarity, and are not necessarily drawn to scale. The dimensions of some elements in the figures may have been exaggerated relative to other elements to help understanding of the present teachings. Furthermore, a particular order in which certain elements, parts, components, modules, steps, actions, events and/or processes are described or illustrated may not be actually required. A person of ordinary skill in the art will appreciate that, for the purpose of simplicity and clarity of illustration, some commonly known and well-understood elements that are useful and/or necessary in a commercially feasible embodiment may not be depicted in order to provide a clear view of various embodiments in accordance with the present teachings.

DETAILED DESCRIPTION

Turning to the Figures and to FIG. 6 in particular, an illustrative diagram of a new needle is shown and generally indicated at 600. The needle 600 includes a shaft 602, a front end bevel 604 at the front end of the shaft 602, a rear end bevel 606 at the rear end of the shaft 602, and a needle hub 608. The shaft 602 extends through and is firmly attached to the needle hub 608. The shaft 602 does not move inside the needle hub 608. The bevel 604 is adapted to penetrate into the body of a patient. The bevel 606 is adapted to penetrate into the cover of a cartridge adapted to be disposed inside the barrel 108. Internal cavity of the barrel 108 is exposed by the opening 110. The shaft 602 incorporates an internal channel running through the entire length of the shaft 602 and through the bevels 604-606 for transmitting liquid. The bevels 604-606 are generally referred to herein as sharp ends of the needle 600.

The needle hub 608 includes a rear needle body portion 610, a front needle body portion 612 and a cap stopper 614 between the rear and front needle bodies 610-612. In one implementation, the rear needle body portion 610, the front needle body portion 612 and the cap stopper 614 are integrally formed. Alternatively, they are separate parts coupled together via, for example, threading or welding.

The rear needle bevel 606 and the rear needle body 610 are adapted to be received by and disposed inside a rear needle cap, such as the rear needle cap 800 shown in FIG. 8. When the needle 600 is in transportation, storage and waiting to be used, the rear needle cap 800 is attached to the needle 600 to protect the rear portion of the shaft 602 extending away from the rear needle body 610.

In addition, the needle 600 incorporates a needle coupling mechanism for attaching the needle 600 to an aspirating syringe, such as the syringe 100. In one implementation, the rear needle body 610 incorporates a female thread for receiving the needle adaptor 114. In such a case, a user of the needle 600 carefully inserts the bevel 606 into the internal channel of the needle adaptor 114 and then firmly attaches the needle 600 to the syringe 100 via the threads of the needle adaptor 114 and the female threads of the rear needle body 610. A left side view of the shaft 602 and the rear needle body 610 is shown in FIG. 12.

Figure 12:
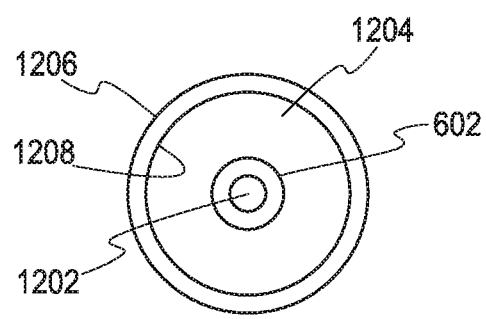
FIG. 12 is a left side view of a new needle in accordance with this disclosure.

Referring to FIG. 12, the internal cavity channel of the shaft 602 is indicated at 1202. The outer surface of the rear needle body 610 is indicated at 1206 while the inner surface of the rear needle body 610 is indicated at 1208. The cavity adapted for receiving the needle adaptor 114 is indicated at 1204. The female thread of the rear needle body 610 is incorporated on the inner surface 1208. The cavity 1204 does not run through the entirety of the needle hub 608. Instead, its depth is properly configured to receive the needle adaptor 114.

Turning back to FIG. 6, the front needle body 612 is adapted to be received by a new front needle cap 700 shown in FIG. 7. When the needle 600 is in transportation or waiting to be used, the cap 700 is attached to the needle 600. In particular, the cap 700 is attached to and encloses the front needle body 612. At this position, the front shaft portion extending away from the front needle body 612 and the bevel 604 are disposed inside the internal cavity 706 of the front needle cap 700. The cap stopper 614 incorporates a larger diameter than those of the needle body portions 610-612 to prevent the caps 700-800 from enclosing too much of the needle hub 608 to damage the bevels 604-606.

The improved needle 600 further incorporates a guiding grove 618 extending along the front needle body 612 and exposed on the outer surface of the front needle body 612, and a locking cavity 616 at the rear end of the guiding grove 618 and exposed on the outer surface of the front needle body 612. The locking receptacle 616 communicates with and extends from the guiding channel 618.

Referring to FIG. 7, a perspective view of the improved front needle cap 700 is shown. The front needle cap 700 includes a cap body 702 enclosing the internal cavity 706 for receiving the front needle body 612 and the needle shaft 602. The front needle cap 700 further incorporates a locking plug 704 extending from the inner surface of the cavity 706 toward the center axis of the cavity 706.

The locking plug 704 is adapted to move along the guiding channel 618 and be disposed inside the locking receptacle 616. When the front needle cap 700 is attached to the needle 600, the locking plug 704 is received by the locking cavity 616. The locking plug 704 and the locking cavity 616 have the same or substantially the same shape for tight interlocking. For example, they are in the shape of a prism. As another example, the locking receptacle 618 and the locking plug 704 are spherical caps.

After a user attaches the needle 600 to the needle adaptor 114 for using the needle 600, the user slightly turns the front needle cap 700 clockwise such that the locking plug 704 is aligned with the guiding channel 618. The user then pulls the front needle cap 700 away from the needle 600 with the locking plug 704 moving inside the guiding channel 618. At this point, the needle 600 is ready for use, such as a dental procedure.

After the use is over, the user attaches the front needle cap 700 back to the needle 600. To do so, she/he first inserts the bevel 604 and the shaft 602 into the cavity 706. Then, she/he aligns the locking plug 704 with the guiding channel 618 before move the needle 600 further inside the front needle cap 700 while the locking plug 704 moves inside the guiding channel 618. Once the locking plug 704 reaches the end of the locking channel 618, she/he slightly rotates the front needle cap 700 counterclockwise such that the locking plug 704 is disposed inside the locking receptacle 616 and no longer aligned with the guiding channel 618.

Thereafter, the user continues to rotate the front needle cap 700 counterclockwise while firmly holding the barrel 108 by a different hand. The rotation unscrews the needle 600 from the needle adaptor 114. During the removal process, the interlocking between the locking cavity 616 and the locking plug 704 avoids the front needle cap 700 from being removed from the needle hub 608. Accordingly, the interlocking mechanism prevents the accidental separation between the front needle cap 700 and the needle 600 right during the recapping process after the needle 600 is used in a procedure.

The locking receptacle 616 includes a side 620 extending away from the guiding channel 618. The direction by which the side 620 extends away from the guiding channel 618 needs to be in the same direction by which the needle 600 is rotated to be detached from the aspirating syringe 100. The direction can be clockwise or counterclockwise, depending on the commercial embodiments. The direction is termed herein as a needle detachment direction. Furthermore, the locking receptacle 616 is said to extend from the guiding channel 618 in the needle detachment direction. During the recapping of the needle 600, the locking plug 704 is against a bottom side 622 of the locking receptacle 616. Therefore, the side 620 prevents the locking plug 704 from moving away from the front needle body 612.

In a further implementation, the front needle body 612 incorporates a tapered front end 904 shown in FIG. 9. In such a case, a protruding line 902 is provided on the tapered front end 904. The guiding line 902 is aligned with the top edge of the guiding channel 618. The guiding line 902 assists the user to align the locking plug 704 with the locking channel 618. Furthermore, the guiding line 902 has an decreasing height toward the cylindrical portion of the front needle body 612 such that the guiding line 902 does not increase the outer diameter or circumference of the cylindrical portion of the front needle body 612.

When the locking plug 704 is disposed inside the locking receptacle 616, the front needle cap 700 cannot move along the shaft 602. The cap stopper 614 is thus not required to practice the present teachings. In other words, with the interlocking mechanism, the present teaching can be practiced without cap stopper 614.

When the user attaches the front needle cap 700 to the needle 600 after its use, she/he still needs to carefully align the sharp front end 604 of the shaft 602 with the cavity 706. A mistake in aligning them can cause the sharp front end 604 to puncture the user's hand and lead to serious heath harm to the user. One conventional solution is that the user attaches the cap 400 to a flat object (such as a square board) through an aperture in the flat object. The flat object has a much larger length and width than the diameter of the cap 400. The user then holds the flat object to align the cap 400 with the sharp end 204 of the needle 200 to avoid accidental puncture by the needle.

Figure 11:
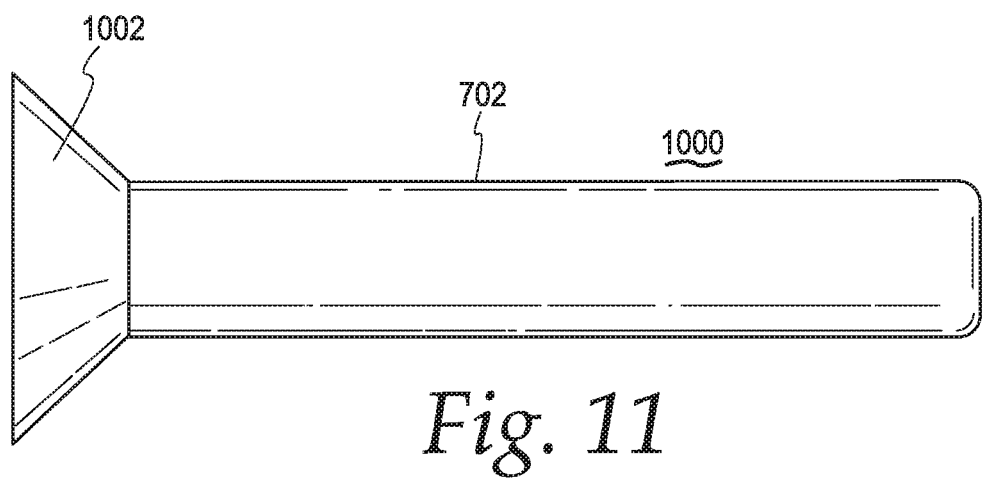
FIG. 11 is a front side view of a new front needle cap in accordance with this disclosure.

An improved front needle cap shown in FIGS. 10-11 solves the problem and avoids the flat object. Turning to FIG. 10, a perspective of an improved front needle cap is shown and generally indicated at 1000. The improved front needle cap 1000 takes the shape of a filling funnel on its opening end. The front circular funnel lip 1002 provides a larger diameter than that of the cavity 706, makes the alignment between the cavity 706 and the needle end 604 easier, and avoids accidental puncture of the user's hand by the sharp end 604 during recapping of the needle 600.

As used herein, the needle 600, the front needle cap 700 and the rear needle cap 800 are collectively referred to as a needle assembly. The needle 600, the front needle cap 1000 and the rear needle cap 800 are a different needle assembly. Needle assemblies are each packaged together and provided to users. Accordingly, the present teachings provide improved needle assemblies.

Obviously, many additional modifications and variations of the present disclosure are possible in light of the above teachings. Thus, it is to be understood that, within the scope of the appended claims, the disclosure may be practiced otherwise than is specifically described above. For example, the funnel lip 1002 can be at different angles to the center axis of the front needle cap body 702. As an additional example, the height of the funnel lip 1002 can vary. As still a further example, when the needle adaptor 114 includes a female thread, the needle hub 608 includes a male thread for attaching the needle 600 to the aspirating syringe 100.

The foregoing description of the disclosure has been presented for purposes of illustration and description, and is not intended to be exhaustive or to limit the disclosure to the precise form disclosed. The description was selected to best explain the principles of the present teachings and practical application of these principles to enable others skilled in the art to best utilize the disclosure in various embodiments and various modifications as are suited to the particular use contemplated. It should be recognized that the words "a" or "an" are intended to include both the singular and the plural. Conversely, any reference to plural elements shall, where appropriate, include the singular.

It is intended that the scope of the disclosure not be limited by the specification, but be defined by the claims set forth below. In addition, although narrow claims may be presented below, it should be recognized that the scope of this invention is much broader than presented by the claim (s). It is intended that broader claims will be submitted in one or more applications that claim the benefit of priority from this application. Insofar as the description above and the accompanying drawings disclose additional subject matter that is not within the scope of the claim or claims below, the additional inventions are not dedicated to the public and the right to file one or more applications to claim such additional inventions is reserved.

What is claimed is:

1. A needle assembly comprising:
   1) a needle having a needle hub and a needle shaft disposed within and running through said needle hub wherein:
      i. said needle hub includes a rear needle body and a front needle body;
      ii. said rear needle body includes a female thread adapted for attaching said needle to a syringe needle adaptor;
      iii. said shaft includes a front end bevel, a rear end bevel and an internal cavity channel extending the entire length of said shaft;
      iv. said front needle body includes a guiding channel exposed on an outer surface of said front needle body, wherein said guiding channel is axial along said front needle body and substantially extends to a distal end of b said front needle body;
      v. said front needle body includes a locking receptacle exposed on said outer surface of said front needle body, connecting to a rear end of said guiding channel and extending away from said guiding channel in a needle detachment direction; and
      vi. said needle hub includes a cap stopper disposed between said rear needle body and said front needle body;
   2) a rear needle cap adapted to be attached to and enclose said rear needle body; and
   3) a front needle cap adapted to be attached to and enclose said front needle body, said front needle cap incorporating a front needle cap cavity and a locking plug, said locking plug extending away from an inner surface of said front needle cap and into said front needle cap cavity, said locking plug adapted to move along said guiding channel and be received by said locking receptacle, wherein said cap stopper incorporated a larger diameter than those of said rear needle body and said front needle body to prevent contact between said rear needle cap and said front needle cap.

2. The needle assembly of claim 1, wherein said front needle cap further incorporates a front funnel lip.

3. The needle assembly of claim 2, wherein said locking plug and said locking receptacle are in a shape of a prism or a spherical cap.

4. The needle assembly of claim 1, wherein said locking plug and said locking receptacle are in a shape of a prism or a spherical cap.

5. A needle assembly comprising:
   1) a needle having a needle hub and a needle shaft disposed within and running through said needle hub wherein:
      a. said needle hub includes a rear needle body and a front needle body;
      b. said rear needle body includes a needle coupling mechanism adapted for attaching said needle to a syringe needle adaptor;
      c. said shaft includes a sharp front end, a sharp rear end and an internal cavity channel extending the entire length of said shaft;
      d. said front needle body includes a guiding channel exposed on an outer surface of said front needle body, wherein said guiding channel is axial along said front needle body and substantially extends to a distal end of b said front needle body;
      e. said front needle body includes a locking receptacle exposed on said outer surface of said front needle body, connecting to a rear end of said guiding channel and extending away from said guiding channel in a needle detachment direction; and
      f. said needle hub includes a cap stopper disposed between said rear needle body and said front needle body;
   2) a rear needle cap adapted to be attached to and enclose said rear needle body; and
   3) a front needle cap adapted to be attached to and enclose said front needle body, said front needle cap incorporating a front needle cap cavity and a locking plug, said locking plug extending away from an inner surface of said front needle cap and into said front needle cap cavity, said locking plug adapted to move along said guiding channel and be received by said locking receptacle, wherein said cap stopper incorporated a larger diameter than those of said rear needle body and said front needle body to prevent contact between said rear needle cap and said front needle cap.

6. The needle assembly of claim 5, wherein said front needle cap further incorporates a front funnel lip.

7. The needle assembly of claim 6, wherein said needle coupling mechanism is a female thread or a male thread.

8. The needle assembly of claim 6, wherein said sharp front end is a bevel.

9. The needle assembly of claim 6, wherein said sharp rear end is a bevel.

10. The needle assembly of claim 6, wherein said locking plug and said locking receptacle are in a shape of a prism or a spherical cap.

11. The needle assembly of claim 5, wherein said needle coupling mechanism is a female thread or a male thread.

12. The needle assembly of claim 5, wherein said sharp front end is a bevel.

13. The needle assembly of claim 5, wherein said sharp rear end is a bevel.

14. The needle assembly of claim 5, wherein said locking plug and said locking receptacle are in a shape of a prism or a spherical cap.

15. A needle assembly comprising:
   1) a needle having a needle hub and a needle shaft disposed within and running through said needle hub wherein:
      i. said needle hub includes a rear needle body and a front needle body;
      ii. said rear needle body includes a needle coupling mechanism adapted for attaching said needle to a syringe needle adaptor;
      iii. said shaft includes a sharp front end, a sharp rear end and an internal cavity channel extending the entire length of said shaft;
      iv. said needle hub incorporates a cap stopper disposed between said rear needle body and said front needle body; and
   2) a rear needle cap adapted to be attached to and enclose said rear needle body; and
   3) a front needle cap adapted to be attached to and enclose said front needle body, said front needle cap incorporating a front needle cap cavity, said front needle cap incorporating a front funnel lip, wherein said cap stopper incorporates a larger diameter than those of said rear needle body and said front needle body to prevent contact between said rear needle cap and said front needle cap.

16. The needle assembly of claim 15, wherein said needle coupling mechanism is a female thread or a male thread.

17. The needle assembly of claim 15, wherein said sharp front end is a bevel and said sharp rear end is a bevel.

18. The needle assembly claim 15, wherein said needle hub further includes a cap stopper disposed between said rear needle body and said front needle body.

* * * * *